United States Patent [19]

Bollinger et al.

[11] 4,108,632
[45] Aug. 22, 1978

[54] USE OF PHTHALANILIC ACIDS TO REGULATE THE GROWTH OF CORN PLANTS

[75] Inventors: Frederic G. Bollinger; John J. D'Amico, both of St. Louis; Dale J. Hansen, St. Charles, all of Mo.

[73] Assignee: Monsanto Company, St. Louis, Mo.

[21] Appl. No.: 753,392

[22] Filed: Dec. 22, 1976

[51] Int. Cl.² ........................... A01N 9/20; A01N 9/14
[52] U.S. Cl. ............................................ 71/115; 71/98
[58] Field of Search .................................... 71/115, 98

[56] References Cited

U.S. PATENT DOCUMENTS 3,658,892  4/1972  Martin et al. .................... 260/518 A

OTHER PUBLICATIONS

Hoffman et al., Science, vol. 109 (1949), p. 588.
Teubner et al., Science, vol. 122 (1955), p. 74.

*Primary Examiner*—Catherine L Mills
*Attorney, Agent, or Firm*—Richard H. Shear; Donald W. Peterson

[57] ABSTRACT

Certain substituted phthalanilic acids and their salts have been found to alter sexual reproduction in corn plants.

6 Claims, No Drawings

USE OF PHTHALANILIC ACIDS TO REGULATE THE GROWTH OF CORN PLANTS

This invention relates to the use of certain substituted phthalanilic acids and salts thereof to alter the sexual reproduction of corn plants. More particularly, the invention contemplates the use of phthalanilic acids having the formula

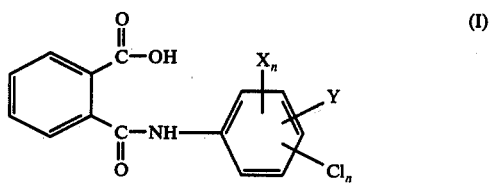

wherein X is halogen, $CF_3$ or lower alkoxy; Y is halogen, $CF_3$, lower alkoxy, phenoxy, $SCH_3$, hydroxyethyl or lower alkyl; and each $n$ is independently 0 and 1; and agriculturally acceptable salts thereof provided that Y cannot be fluorine in the 3 position, when $n$ is 0.

As used herein, the term "agriculturally acceptable salts" includes but is not limited to alkali metal, substituted amine, such as isopropylamine and triethylamine and ammonium salts.

The term "lower alkyl" and "lower alkoxy" is understood to include those alkyl and alkoxy radicals having from one to four carbon atoms inclusive.

The compounds of the invention may be prepared in accordance with known procedures. U.S. Pat. No. 3,658,892 discloses the preparation of the present compounds by reacting phthalic acid or phthalic acid anhydride with the appropriate aniline.

For example, the compounds of the invention may be prepared by adding 0.1 mole of the appropriate substituted aniline to a stirred slurry containing 0.1 mole of the phthalic acid anhydride in 100–125 ml. of chloroform. After stirring at ambient temperatures for about 24 hours, the precipitate is collected by filtration and air-dried.

In accordance with the above procedure, the following compounds have been prepared.

The compounds represented by Formula I above have been found to be effective in altering the development of both the male (tassel) and female (ear) reproductive components of corn plants. As used herein, the alteration of the "development of the reproductive component" of the corn plant is understood to mean the modification of the normal sequential development of said component to maturity. Such modifications are most readily observed as inhibition of tassel growth, inhibition of lateral tassel branches, alteration in ear numbers, shape, position, kernel numbers, speed of silking, etc.

The invention contemplates the alteration of the development of the reproductive components of healthy corn plants by applying an effective, non-lethal amount of phthalanilic acids of Formula I to said corn plant before or during the early stages of the development of said reproductive component referred to herein as reproductive differentiation. As a result of such application, tassel size can be reduced or eliminated, thus reducing or eliminating the labor required by hybrid seed corn producers to manually detassel said corn plants. Additionally, the amount of seed per unit area of land may be increased by applying an effective amount of the active ingredient before or during the early stages of the development of said ear.

As used herein, the term "active ingredient" refers to the phthalanilic acids of Formula I.

In accordance with the novel aspects of the present invention, compounds 1–23 were tested in accordance with the following procedure.

EXAMPLE A

A-619 variety corn plants were grown and thinned to obtain a uniform population. All weak or late plants were removed before chemical application. The active ingredient was formulated by adding 50 or 100 mg. of the active ingredient to 7.5 ml. of acetone and 7.5 ml. of water. 0.25% Tween 20 was added as a surfactant. Utilizing a Devilbiss #152 sprayer, the corn plants were sprayed during the early stages of reproductive differentiation at a rate of 10 mg. per plant or 20 mg. per plant.

Results were analyzed by comparing the treated plants to control plants which were not chemically treated. Chemicals were considered to be active in altering the reproductive development of the corn plant if treatment resulted in an inhibition of at least 25 percent

| | Analysis | |
|---|---|---|
| Compound | Calculated | Found |
| (1) 2-trifluoromethyl-4-chloro-phthalanilic acid | C, 52.42; H, 2.64; N, 4.08 | C, 52.26; H, 2.67; N, 4.12 |
| (2) 4-phenoxy-phthalanilic acid | C, 72.06; H, 4.54; N, 4.20 | C, 72.29; H, 4.43; N, 4.30 |
| (3) 2,5-dichloro-phthalanilic acid | N, 4.52; Cl, 22.86 | N, 4.65; Cl, 23.02 |
| (4) 3,5-di(trifluoromethyl)phthalanilic acid | N, 3.71; F, 30.21 | N, 3.65; F, 30.00 |
| (5) 4-bromo-2-methyl-phthalanilic acid | N, 4.19; Br, 23.91 | N, 4.21; Br, 23.80 |
| (6) 5-bromo-2-trifluoromethyl-phthalanilic acid | N, 3.60; Br, 20.58 | N, 3.62; Br, 20.74 |
| (7) 3,5-dimethoxy-phthalanilic hthalanilic acid | C, 63.77; H, 5.01; N, 4.64 | C, 63.85, H, 4.93; N, 4.77 |
| (8) 4-methoxy-phthalanilic acid | C, 66.41; H, 4.83 | C, 66.40; H, 4.86 |
| (9) 4-trifluoromethyl-phthalanilic acid | C, 58.26; H, 3.26 | C, 59.02; H, 2.99 |
| (10) 3-trifluoromethyl-phthalanilic acid | C, 58.26; H, 3.26 | C, 58.50; H, 3.25 |
| (11) 4-fluoro-phthalanilic acid | N, 5.40; F, 7.33 | N, 5.46; F, 7.10 |
| (12) 2-chloro-5-trifluoromethyl-phthalanilic acid | C, 52.42; H, 2.64; N, 4.08 | C, 52.46; H, 2.64; N, 4.10 |
| (13) 2-methyl-4-bromo-5-chloro-phthalanilic acid | C, 48.87; H, 3.00; N, 3.80 | C, 49.06; H, 3.05; N, 3.67 |
| (14) 3-(1'-hydroxyethyl)phthalanilic acid | C, 67.36; H, 5.30; N, 4.91 | C, 67.28; H, 5.19; N, 4.76 |
| (15) 3,4-difluoro-phthalanilic acid | N, 5.06; F, 13.71 | N, 5.09; F, 13.68 |
| (16) 2-fluoro-5-trifluoromethyl-phthalanilic acid | N, 4.28; F, 23.22 | N, 4.13; F, 23.06 |
| (17) 2-bromo-5-trifluoromethyl-phthalanilic acid | N, 3.60; Br, 20.58 | N, 3.69; Br, 20.61 |
| (18) 4-methylthio-phthalanilic acid | N, 4.87; S, 11.16 | N, 5.03; S, 11.37 |
| (19) 2,5-dimethoxy-phthalanilic acid | C, 63.77; H, 5.01; N, 4.64 | C, 64.00; H, 5.07; N, 4.74 |
| (20) 3-methoxy-phthalanilic acid | C, 66.41; H, 4.83 | C, 66.51; H, 4.86 |
| (21) 2-methoxy-phthalanilic acid | C, 66.41; H, 4.83 | C, 66.37; H, 4.83 |
| (22) 3,5-dichloro-phthalanilic acid | N, 4.52; Cl, 22.87 | N, 4.49; Cl, 22.68 |
| (23) 2-fluoro-phthalanilic acid | N, 5.40; F, 7.33 | N, 5.37; F, 7.12 | of the lateral tassel formation when compared to the control plants.

In accordance with the above procedure, compounds 1-8 and 22 were found to be effective in inhibiting from 50 to 74 percent of the lateral tassel development. The remaining compounds were found to be effective in inhibiting from 25 to 49 percent of the lateral tassel development. In addition, flowering was inhibited as illustrated in Table I.

Table I

| Compound | cm. of Flowers |
|---|---|
| Control | 224 |
| 10 | 188 |
| 9 | 176 |
| 1 | 77 |
| 6 | 29 |
| 7 | 78 |

EXAMPLE B

In another test, 2-trifluoromethyl-4-chloro phthalanilic acid was applied to corn plants as a formulation described above. Responses noted included alteration of ear height, increased speed of silking and partial sterility. Table II illustrates the responses noted.

Table II

| Rate of Treatment kilos/hectare | | | Ear Height | Percent of Male |
|---|---|---|---|---|
| Day 9[a] | Day 12[a] | Day 15[a] | (cm) | Sterility |
| 0 | 0 | 0 | 48 | 0 |
| 1.12 | 1.12 | 0 | 59 | 90 |
| 1.12 | 0 | 1.12 | 66 | 89 |
| 1.12 | 0.56 | 0 | 74 | 79 |
| 1.12 | 0 | 0.56 | 57 | 93 |
| 0.56 | 1.12 | 0 | 63 | 10 |
| 0.56 | 0 | 1.12 | 53 | 93 |
| 0.56 | 0.56 | 0 | 64 | 80 |
| 0.56 | 0 | 0.56 | 64 | 89 |

[a]from seedling emergence.

As exemplified above, the invention contemplates the application of the phthalanilic acids before or during the early stages of the reproductive differentiation. Reproductive differentiation occurs at different times depending upon the variety of corn plant as well as environmental factors. For example, male reproductive differentiation of Gaspé corn begins during kernel formation while reproduction differentiation of A-619 corn begins within the first 8 to 12 days after seedling emergence. The determination of when reproductive differentiation occurs is within the skill of the art. By way of example and for purposes of illustration only, applications for most varieties used in the Midwest of the United States ranging from 3 to 25 days after seedling emergence are desirable. Varieties used in foreign countries may require applications ranging from 1 to 40 days from seedling emergence. The following example illustrates that for A-619 variety corn, applications between 7 to 12 days after seedling emergence are preferred.

EXAMPLE C

Corn, A-619 variety, was planted in plots at a rate of 64,000 plants per hectare. These plants were treated at rates ranging from 0.56 to 1.68 kilos per hectare with a formulation of compound 1, 50 percent acetone and 0.25 percent Tween 20 at a rate of 320 liters per hectare. Some applications were made early, on or before 12 days after seedling emergence. Other applications were made late, after 12 days from seedling emergence. After harvest, the yields of the treated plants were compared to those of the untreated control plants. Table III illustrates the results of this test.

Table III

| Control Yields | Grams/Plot Early Applicaton | Late Applications |
|---|---|---|
| 1300 | 2000 | 1330 |
| 2060 | 1900 | 1470 |
| 1940 | 1800 | 1620 |
| 1650 | 1900 | 1460 |
| 1740 | 2260 | 1410 |
| 1700 | 1930 | 1520 |
| 1910 | 1500 | |
| 1810 | 2400 | |
| 1850 | | |
| 1770 | | |
| Mean 1773 | 1961 | 1468 |

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surfaceactive agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 1 to 99 parts active ingredient, about 1 to 50 parts surface-active agent and about 4 to 94 parts solvents, all parts being by weight based on the total weight of the composition.

In selecting the appropriate rate of application of the active ingredient, it will be recognized that precise rates will also be dependent upon the mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above.

This invention, however, does not contemplate the use of phytotoxic rates which exert a herbicidal effect. In addition, it will be recognized that single or multiple applications may be used to exert the desired response.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows:

1. A method for altering the development of the reproductive components of a corn plant which comprises applying to said corn plant before or during the early stages of reproductive differentiation an effective, non-lethal amount of a compound having the formula

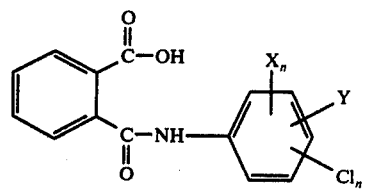

wherein X is halogen, $CF_3$ or lower alkoxy; Y is halogen, $CF_3$, lower alkoxy, phenoxy, $SCH_3$, hydroxyethyl, or lower alkyl; each $n$ is independently 0 or 1; and agriculturally acceptable salts thereof provided that Y cannot be fluorine in the 3 position, when $n$ is 0.

2. The method of claim 1 wherein $n$ is 0.
3. The method of claim 1 wherein X is halogen or $CF_3$; and Y is halogen or $CF_3$.
4. The method of claim 1 wherein said compound is 2-trifluoromethyl-4-chloro-phthalanilic acid.
5. The method of claim 1 wherein said reproductive component is the male component.
6. The method of claim 1 wherein said reproductive component is the female component.

* * * * *